United States Patent [19]

Maier et al.

[11] Patent Number: 5,674,852
[45] Date of Patent: Oct. 7, 1997

[54] WATER-SOLUBLE RETINOIDS

[75] Inventors: Thomas Maier, Schliengen; Helmut Luther, Grenzach-Wyhlen, both of Germany

[73] Assignee: Ciba-Geigy Corporation, Tarrytown, N.Y.

[21] Appl. No.: 318,870

[22] PCT Filed: Apr. 10, 1993

[86] PCT No.: PCT/EP93/00878
§ 371 Date: Oct. 18, 1994
§ 102(e) Date: Oct. 18, 1994

[87] PCT Pub. No.: WO93/21195
PCT Pub. Date: Oct. 28, 1993

[30] Foreign Application Priority Data

Apr. 21, 1992 [CH] Switzerland ............ 01 282/92

[51] Int. Cl.⁶ ............ A61K 31/70; C07H 1/00; C07H 15/00
[52] U.S. Cl. ............ 514/25; 536/4.1; 536/18.5; 536/18.6; 536/122; 536/124
[58] Field of Search ............ 514/25; 536/4.1, 536/122, 18.5, 18.6, 124

[56] References Cited

U.S. PATENT DOCUMENTS

| | | | |
|---|---|---|---|
| 4,457,918 | 7/1984 | Holick et al. | 424/180 |
| 4,565,863 | 1/1986 | Bollag et al. | 536/18.2 |
| 5,091,371 | 2/1992 | Lakeuchi et al. | 514/33 |

FOREIGN PATENT DOCUMENTS

| | | |
|---|---|---|
| 2556348 | 6/1985 | France. |
| WO9014093 | 11/1990 | WIPO. |

OTHER PUBLICATIONS

Internation Journal for Vitamin and Nutrition Research Bd. 61, 1991, Seiten pp. 258–263, A B Barua et al.

Primary Examiner—Elli Peselev
Attorney, Agent, or Firm—Kevin T. Mansfield

[57] ABSTRACT

The present invention relates to novel water-soluble sugar retinoids in which the sugar radical carries at least one sulfate group, and to their preparation and use thereof as medicaments and in cosmetic sector.

23 Claims, No Drawings

WATER-SOLUBLE RETINOIDS

The present invention relates to novel water-soluble sugar retinoids in which the sugar radical carries at least one sulfate group, and to their preparation and the use thereof as medicaments and in the cosmetic sector.

Retinoic acid derivatives are commonly used in the field of dermatology. Thus keratinising epithelial tissue can be converted by retinoic acid or derivatives thereof into tissue of normally differentiated cells. The retinoids exert a protective action against chemically, photochemically or virally induced carcinogenesis and assume protective functions in cell division. Retinoic acid itself is water-insoluble and is therefore usually converted into a water-soluble form for ease of handling.

Aromatic retinoids having a saccaride or aminosaccharide radical, and which are suitable dermatalogical agents for use in pharmaceuticals and cosmetics, are disclosed in U.S. Pat. No. 4,565,863. For toxicological reasons, such aromatic retinoids are sought to be avoided.

Accordingly, the invention relates to water-soluble aliphatic derivatives of retinoic acid. These novel retinoids are retinoic acid esters of formula (I)

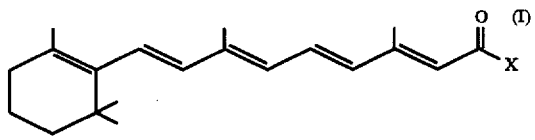

wherein X is a sugar residue attached at an oxygen atom, i.e. a mono-, di- or oligosaccharide which is sulfated at one or more than one OH group.

The double bonds in the retinoic acid radical may be in cis- or trans-configuration, the all-trans-form being preferred.

Oligosaccharides containing more than two sugar units may suitably be in particular compounds such as streptomycin, neuramic acid, fucose, α,β,γ-cyclodextrin, raffinose or short-chain degradation products of amylose or cellulose.

The sugar radical is preferably a mono- or disaccharide which is derived from ribose, arabinose, xylose, glucose, mannose, galactose, lactose, saccharose, trehalose, cellobiose, maltose, fructose or derivatives thereof, wherein at least one OH group is substituted by $OSO_3M$.

Suitable derivatives of these sugars include:

desoxy sugar; the lactones of the corresponding sugar acids such as gluconic acid γ-lactone which in turn may be esterified by $C_1$—$C_4$alkyl; uronic acids; amino sugars having an unsubstituted amino group, typically glucosamine, fructosamine, galactosamine, or having a $C_1$—$C_6$alkyl— or $C_1$—$C_6$acetyl-substituted amino group, e.g. aminoethylglucosides, aminoethyl-2-deoxy-2-aminoglucoside, N-acetylaminoglucoside; sugars in which the OH groups are substituted by one or more than one $C_1$—$C_4$alkoxy group, e.g. methyl or ethyl glucose, substitution by $C_1$—$C_4$alkylene bridges also being possible; keto-sugar acids such as ascorbic acid; sugars in which the OH groups are mono- or polyacetylated, typically glucose acetate or 2,3,4-tri-O-acetylglucose; or sugars carrying several different substituents, e.g. neuraminic acid.

Particularly preferred sugars are glucose, galactose, mannose or derivatives thereof.

The aforementioned sugar radicals may also be in the form of racemates or any mixtures of the (L)- and (D)-configuration as well as in the form of the pure (L)- or (D)-isomers. The natural (D)-configuration is preferred.

The sulfate group introduced into the sugar radiacal may be in the form of the free acid or the salt $OSO_3M$. The counterion M may suitably be hydrogen, an alkali metal ion, an alkaline earth metal ion or $NZ_4$, where Z is hydrogen; $C_1$—$C_4$alkyl such as methyl or ethyl; $C_2$—$C_4$hydroxyalkyl such as 2-hydroxyethyl; or aryl. Compounds in which M is hydrogen or an alkali metal ion are preferred, with hydrogen, sodium and potassium being especially preferred.

Compounds of formula Ia, Ib or Ic are of particular importance:

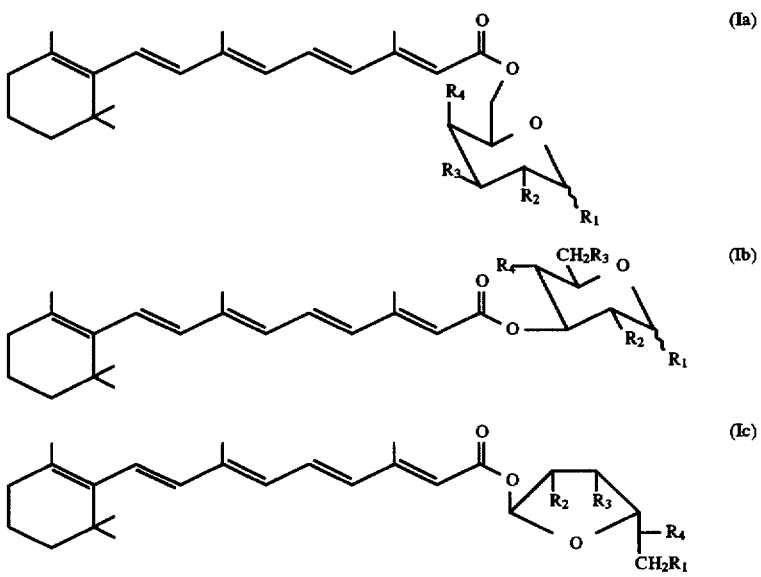

wherein
$R_1$, $R_2$, $R_3$ and $R_4$ are OH, $OSO_3M$, $C_1$—$C_4$alkoxy, $C_1$—$C_3$—COO—, or two of these radicals taken together are a O—$C_1$—$C_4$—O—alkylene bridge, and with the proviso that at least one radical is $OSO_3M$;
M is hydrogen, an alkali metal ion, an alkaline earth metal ion or $NZ_4$;

Z is hydrogen, $C_1$—$C_4$alkyl, $C_2$—$C_4$alkoxy or aryl;
as well as the isomers of the compounds (Ia) and (Ib) in which the saccharide moiety is in the furanose form.

Compounds of formulae Ia, Ib and Ic, wherein M is hydrogen, sodium or potassium, merit special interest.

The compounds of formulae Ia, Ib and Ic, wherein at least one of the substituents $R_1$, $R_2$, $R_3$ and $R_4$ is $OSO_3Na$ and the others are OH, are especially preferred.

The novel compounds of formula (I) are prepared by
a) converting retinoic acid into a reactive derivative,
b) adding a mono-, di- or oligosaccharide, and
c) sulfating some or all of the free OH groups.

The reaction conditions are normally so chosen that the amount of monosulfated sugar is from 50–100% and, preferably, 60–80%.

To enhance its reactivity, the retinoic acid can be converted into a reactive derivative such as an imidazolide, a mixed anhydride or an acid chloride. The acid chloride is preferred. This conversion is preferably carried out with chloroenamine or dimethylchloroformamidininm chloride, using any solvent which is inert to the chlorinating reagent and which at least partially dissolves the retinoic acid, conveniently selected from among ethers, amides, aromatic hydrochlorides, esters, halogenated hydrocarbons, nitriles and sulfoxides. Typical examples of such solvents are methylene chloride, dimethyl formamide, toluene, ethyl acetate, acetonitrile, dimethyl sulfoxide and hexane.

To obtain the retinoic acid esters of formula I, Ia, Ib or Ic, the sugar can be used in already derivatised form or it is derivatised after the linkage to the retinoic acid or after the sulfation. It is preferred to use sugars in which the OH groups that are not to be esterified are provided with protective groups so as to achieve a selective linkage of the sugar to the acid chloride. The protective groups used for this purpose are normally diol protective groups such as isopropylidene, benzylidene or ethylene protective groups, and they are prepared in known manner. After the linkage of the sugar to the retinoic acid, these groups can be removed again in known manner.

The reaction of the sugar with the retinoic acid derivative preferably takes place under the same conditions as are used for the derivatisation of the retinoic acid, and a base such as pyridine can be added to promote the reaction.

The invention further relates to the reaction of unprotected or partially unprotected retinoic acid esters of formula (II)

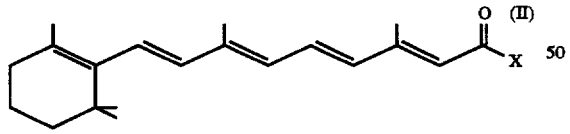

wherein X is a mono-, di- or oligosaccharide which is attached at an oxygen atom and carries at least one free OH group, with a sulfating agent. The reaction is preferably carried out in the temperature range from −10° C. to +10° C. with a conventional sulfating agent in a solvent such as acetone, methylene chloride, dimethyl formamide, toluene, ethyl acetate, acetonitrile, dimethyl sulfoxide or hexane. Sulfating agents which may suitably be used are trialkylsilyl esters of chlorosulfonic acid, such as trimethylsilyl chlorosulfonate, or $SO_3$-pyridine complexes.

It has been found that the compounds of formula (I) can be used for the cosmetic and pharmacological treatment of the eyes or skin, for example for tautening and rejuvenating the skin, for the treatment of acne, psoriasis, neoplasms, dermatoses, as well as for preventive treatment to provide protection from ultraviolet radiation.

For pharmaceutical application, the compounds of formula (I) are formulated with conventional carriers.

Topical application is preferred. Such application comprises treating the skin with an effective amount of the compound of formula (I).

A pharmaceutical or cosmetic composition containing a compound of formula (I) may be administered or applied in the form of tablets, granules, capsules, dragées, ointments, creams, tinctures, lotions, solutions, suspensions, hydrogels, liposomes or foam sprays.

Suitable carriers include mixtures of different emulsifiers, dispersants, stabilisers, perfume oils, antioxidants, thickeners, diluents, humectants, fillers, salts for changing the osmotic pressure, and buffers. Typical examples of such carriers are gelatin, lactose, starch, fatty acid salts, talcum, gum arabic, polyalkylene glycols and other non-toxic excipients.

The concentration of active ingredient may be from 0.01 to 5% by weight, depending on the dosage form.

The following examples illustrate the invention.

EXAMPLE 1

—Linkage of retinoic acid to 1,2:3,4-diisopropylidene-α-D-galactopyranose

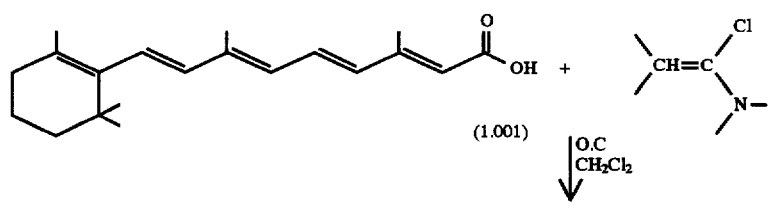

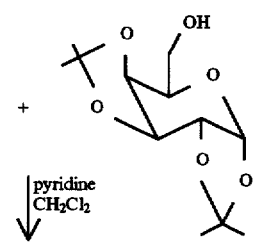
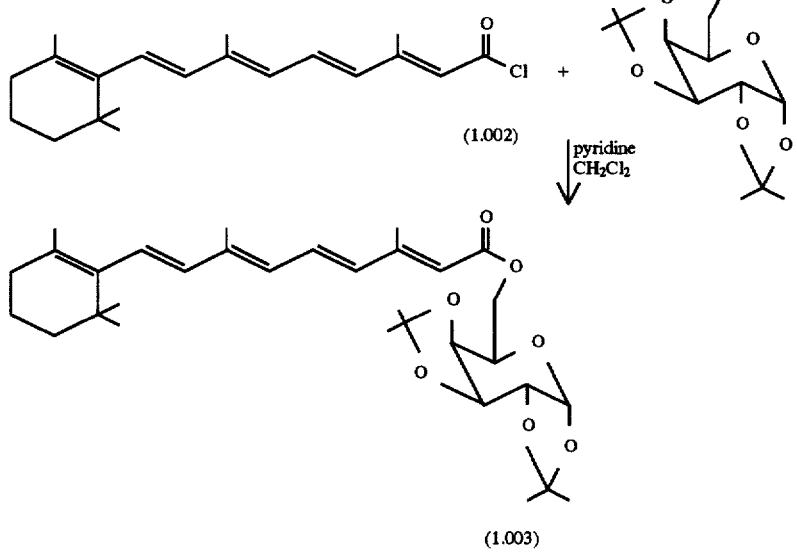

21 g of all-trans-retinoic acid (1.001) are suspended, under nitrogen, in 250 ml of methylene chloride. With stirring, 9,9 ml of chloroenamine are slowly added to the suspension. The clear orange solution is stirred for a further 30 minutes at 0° C. To this solution is added a solution of 1,2:3,4-diisopropylidene-α-D-galactopyranose in 70 ml of methylene chloride and 11 ml of pyridine. After this addition, the ice bath is removed and stirring is continued for another hour. For working up, the solution is concentrated to dryness and the residue is taken up in petroleum/ethyl acetate (15/1) and purified over a silica gel column with petroleum ether/ethyl acetate (15/1). The yield of all-trans-1,2:3,4-diisopropylidene-6-retinoyl-α-D-galactopyranose (1.003) is from 73 to 87%.

—Removal of the protective groups 25 g of 1,2:3,4-diisopropylidene-6-retinoyl-α-D-galactopyranose (1.003) are dissolved in 200 ml of tetrahydrofuran. Then 20 ml of 2N sulfuric acid are added and the reaction mixture is refluxed for 12 hours. For working up, the reaction solution is neutralised with sodium hydrogencarbonate, and the product is extracted with methylene chloride, concentrated to dryness on a rotary evaporator and taken up in methylene chloride/methanol (7/1) and purified over a silica gel column with methylene chloride/methanol (7/1).

The yield of product of formula (1.004) is 79%.

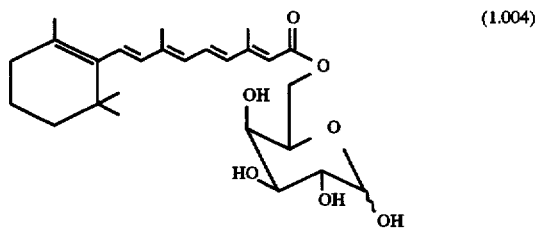

—Sulfation 25 g of a compound of formula (1.004) are dissolved in 100 ml ethyl acetate and the solution is cooled under nitrogen in an ice bath to 0° C. With stirring, 4.7 ml of trimethylsilyl chlorosulfonate are added dropwise and the reaction mixture is stirred for 1 hour at 0° C. and for 30 minutes at room temperature.

For working up, the same volume of water is added and the yellow aqueous phase is separated and adjusted to pH 7 with 2.5 g of sodium hydrogencarbonate. The aqueous phase is freeze-dried, giving up to 90% of a mono- or polysulfated product of formula (1.005)

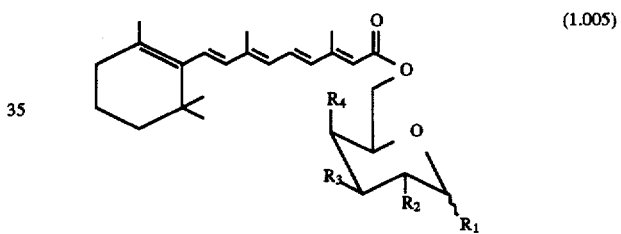

wherein at least one of $R_1$, $R_2$, $R_3$ and $R4$ is $OSO3Na$ and the others are OH, and the sugar radical may be in the furanose form.

The protected α-D-galactopyranose of Example 1 is replaced with the following sugars (unprotected or in suitably protected form): ribose, arabinose, xylose, lactose, saccharose, trehalose, cellobiose, maltose, fructose, neuraminic acid, fucose, α,β,γ-cyclodextrin or raffinose, to give water-soluble derivatives of retinoic acid which can be used for the cosmetic and pharmacological treatment of the eyes or skin.

EXAMPLE 2

In accordance with the general procedure described in Example 1, reaction of all-trans-retinoic acid (1.001) and 2,3:5,6-di-O-isopropylidene-α-D-mannofuranose using 0.03 mol of a $SO_3$-pyridine complex as sulfating reagent gives a compound of formula (1.006)

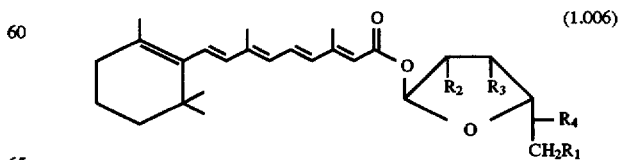

wherein at least one of $R_1$, $R_2$, $R_3$ and $R_4$ is $OSO_3Na$ and the others are OH.

EXAMPLE 3

In accordance with the general procedure described in Example 1, reaction of all-trans-retinoic acid (1.001) and 1,2:5,6;di-O-isopropylidene-α-D-glucopyranose gives a compound of formula (1.007)

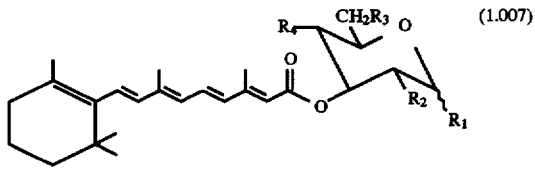

wherein at least one of $R_1$, $R_2$, $R_3$ and $R_4$ is $OSO_3Na$ and the others are OH, and the sugar radical may also be in the furanose form.

EXAMPLE 4

A cream of the following composition is prepared 0.05% of the compound of formula (1.005) of Example 1
2.00% of Amphisol®
2.50% of stearic acid
3.50% of glyceryl myristate
5.00% of isopropyl myristate
3.00% of 1,2-propylene glycol
0.10% of triethanolamine
0.55% of sodium hyalurate
0.02% of propyl parabene
0.18% of methyl parabene
perfume oils as required, and demineralised water to make up 100%

The triethanolamine, sodium hyalurate, parabene, propylene glycol and water are heated to 75° C. and a mixture of the fat-soluble components, also heated to 75° C., is added, and the entire mixture is homogenised. After cooling, with stirring, to 40° C., the sulfo-monosaccharide retinoic acid ester (1.005) and optional perfume oils are added.

EXAMPLE 5

The procedure of Example 4 is repeated, but using a compound of formula (1.006) of Example 2 as monosaccharide.

EXAMPLE 6

The procedure of Example 4 is repeated, but using a compound of formula (1.007) of Example 3 as monosaccharide.

EXAMPLE 7

A transparent hydrogel of the following composition is prepared:

0.1% of the compound of formula (1.005) Example 1
20.0% of 1,2-propylene glycol
20.0% of isopropanol
2.0% of acrylic acid polymer
3.0% of triethanolamine
perfume oils as required, and demineralised water to make up 100%

The acrylic acid polymer and water are dispersed and the dispersion is neutralised with triethanolamine. The sulfo-monosaccharide retinoic acid ester (1.005) is dissolved in a mixture of isopropanol and propylene glycol and the solution is mixed with other components to a gel.

EXAMPLE 8

The procedure of Example 7 is repeated, but using a compound of formula (1.006) of Example 2 as monosaccharide.

EXAMPLE 9

The procedure of Example 7 is repeated, but using a compound of formula (1.007) of Example 3 as monosaccharide.

EXAMPLE 10

A foam spray of the following composition is prepared:

0.03% of the compound of formula (1.005) of Example 1
5.00% of 1,2-propylene glycol
1.70% of cetyl alcohol
1.00% of paraffin oil, viscous
2.00% of isopropyl myristate
2.40% of Cetomacrogol 1000®
1.50% of sorbitan monostearate
0.18% methyl parabene
0.10% propyl parabene
0.10% of Chemoderm 314®
perfume oils as required, and demineralised water to make up 100%

Cetyl alcohol, paraffin oil, isopropyl myristate, Cetomacrogol 1000® and sorbitan stearate are fused and the methyl- and propyl parabene, dissolved in propylene glycol, and hot water are added at 75° C. and the mixture is homogenised. After cooling to 40° C., the sulfo-monosaccharide retinoic acid ester (1.005), Chemoderm 314® and optional perfume oils are added. 20 ml of the mixture are filled into an aluminium lacquer-coated container which is closed with a valve and filled with propellant gas under pressure.

EXAMPLE 11

The procedure of Example 10 is repeated, but using a compound of formula (1.006) of Example 2 as monosaccharide.

EXAMPLE 12

The procedure of Example 10 is repeated, but using a compound of formula (1.007) of Example 3 as monosaccharide.

What is claimed is:

1. A retinoic acid ester of formula (I)

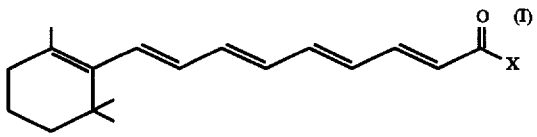

wherein X is a radical of a mono-, di- or oligosaccharide which is sulfated at one or more than one OH group and which is attached to the retinoic acid residue via an oxygen atom.

2. A compound according to claim 1, wherein the retinoic acid radical is in the all-trans form.

3. A compound according to claim 1, wherein
   X is a mono- or disaccharide which is derived from ribose, arabinose, xylose, glucose, mannose, galactose, lactose, saccharose, trehalose, cellobiose, maltose, or fructose and at least one OH group is substituted by $OSO_3M$;

M is hydrogen, an alkali metal ion, an alkaline earth metal ion or $NZ_4$;

Z is hydrogen, $C_1$—$C_4$alkyl or $C_2$—$C_4$hydroxyalkyl.

4. A compound according to claim 3, wherein X is glucose, galactose or mannose.

5. A compound according to claim 3, wherein M is hydrogen or an alkali metal ion.

6. A compound according to claim 3, wherein M is hydrogen, sodium or potassium.

7. A compound according to claim 1, wherein at least one OH group is substituted by $OSO_3M$ and the remaining OH groups are each independently of one another unsubstituted or substituted by $C_1$—$C_4$alkoxy, $C_1$—$C_3$—COO—, or two OH groups taken together may be substituted by a O—$C_1$—$C_4$—O—alkylene bridge.

8. A compound of formula Ia, Ib or Ic

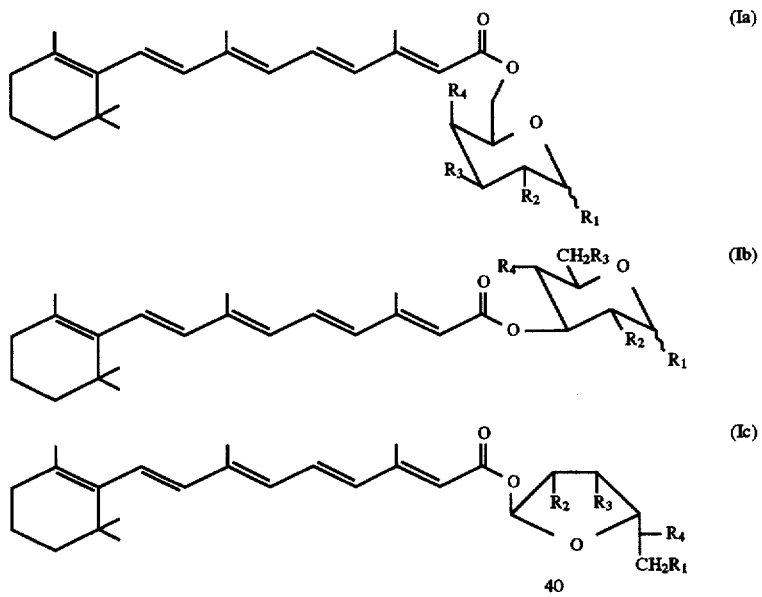

wherein $R_1$, $R_2$, $R_3$ and $R_4$ are OH, $OSO_3M$, $C_1$—$C_4$alkoxy, $C_1$—$C_3$—COO—, or two of these radical taken together are a O—$C_1$—$C_4$—O—alkylene bridge, and with the proviso that at least one radical is $OSO_3M$;

M is hydrogen, an alkali metal ion, an alkaline earth metal ion or $NZ_4$;

Z is hydrogen, $C_1$—$C_4$alkyl or $C_2$—$C_4$alkoxy;

or an isomer of the compounds (Ia) and (Ib) in which the saccharide moiety is in the furanose form.

9. A compound according to claim 8, wherein M is hydrogen, sodium or potassium.

10. A compound according to claim 8, wherein at least one of the substituents $R_1$, $R_2$, $R_3$ and $R_4$ is $OSO_3Na$ and the others are OH.

11. A process for the preparation of a compound of formula (1) according to claim 1 which comprises a) reacting retinoic acid with a compound capable of converting the retinoic acid into the corresponding imidazolide, mixed anhydride or acid chloride, b) reacting a mono-, di- or oligosaccharide containing free OH groups with the imidazolide, mixed anhydride or acid chloride of retinoic acid obtained in step a) and c) reacting the product obtained in step b) and containing at least one free OH group with a sulfating agent.

12. A process according to claim 11, which comprises converting retinoic acid into an acid chloride.

13. A process according to claim 12, which comprises converting retinoic acid into an acid chloride with chloroenamine or dimethylchloroformamidinium chloride.

14. A process according to claim 13, which comprises carrying out reaction step a) with chloroenamine.

15. A process according to claim 11, wherein the mono-, di- or oligosaccharide in step b) has one or more protective groups.

16. A process according to claim 15, wherein diol protective groups are the protective groups for the saccharide.

17. A process according to claim 15, which comprises removing the protective groups for the saccharide after step b).

18. A process for the preparation of a compound of formula (I)

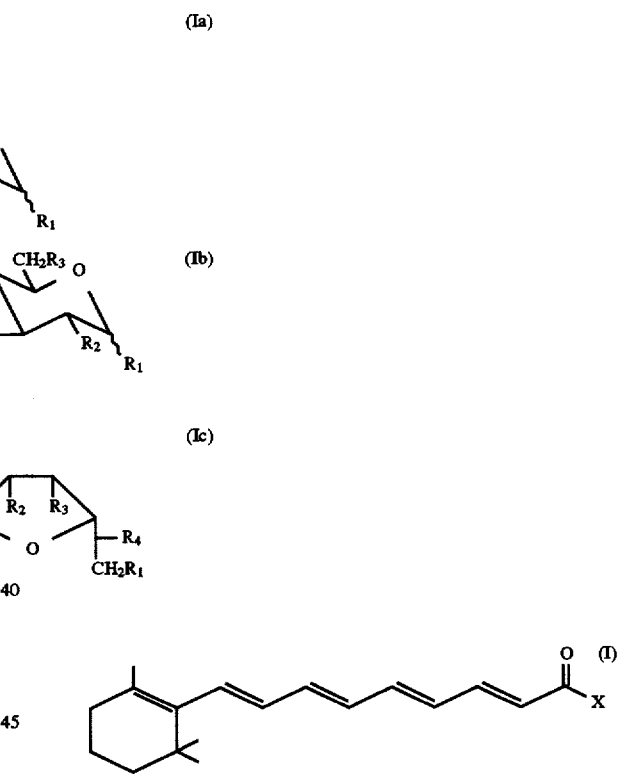

wherein X is a radical of a mono-, di- or oligosaccharide which is sulfated at one or more than one OH group and which is attached to the acid residue via an oxygen atom, which comprises reacting a compound of formula (II)

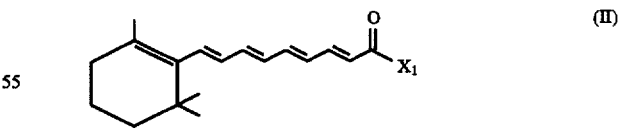

wherein $X_1$ is a radical of a mono-, di- or oligosaccharide which carries at least one free OH group, with a sulfating agent.

19. A process according to claim 11, wherein the sulfating agent is a trialkylsilyl ester of chlorosulfonic acid or a $SO_3$-pyridine complex.

20. A pharmaceutical or cosmetic composition comprising an effective amount of a compound as claimed in claim 1 and a pharmaceutically or cosmetically acceptable carrier.

21. A method for the treatment of acne, psoriasis, skin neoplasms or dermatoses or for treatment to provide protection from ultraviolet radiation, which comprises administering to a host in need of such treatment a pharmaceutically acceptable composition incorporating therein an effective amount of a compound as claimed in claim 1.

22. A method according to claim 21 which comprises topical application of the composition.

23. A compound according to claim 3 in which X is a derivative of a radical of a mono- or disaccharide selected from the group consisting of desoxy sugars, gluconic acid γ-lactone, gluconic acid γ-lactone esterified by $C_1$—$C_4$alkyl, uronic acids, amino sugars having an unsubstituted amino group, amino sugars having a $C_1$—$C_6$alkyl- or $C_1$—$C_6$acetyl-substituted amino group, sugars in which the OH groups are substituted by one or more than one $C_1$—$C_4$alkoxy group, keto sugars, sugars in which the OH groups are mono- or polyacetylated, and neuraminic acid.

* * * * *

UNITED STATES PATENT AND TRADEMARK OFFICE
CERTIFICATE OF CORRECTION

PATENT NO. : 5,674,852
DATED : OCTOBER 7, 1997
INVENTOR(S) : MAIER ET AL.

It is certified that error appears in the above-indentified patent and that said Letters Patent is hereby corrected as shown below:

Columns 8 and 10, claims 1 and 18, please replace Formula (I) with the following:

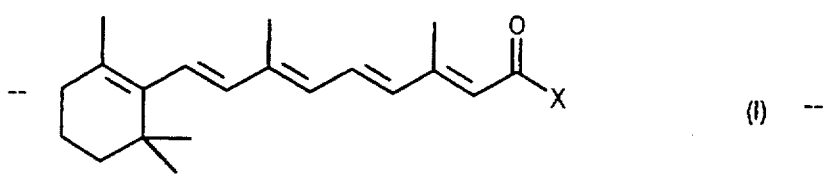

Column 10, claim 18, please replace Formula (II) with the following:

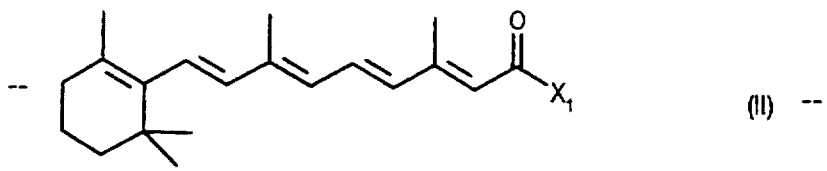

Signed and Sealed this

Twenty-first Day of July, 1998

*Attest:*

BRUCE LEHMAN

*Attesting Officer*     Commissioner of Patents and Trademarks